United States Patent
Mishima et al.

(10) Patent No.: US 10,180,111 B2
(45) Date of Patent: Jan. 15, 2019

(54) GAS SENSOR CONTROL DEVICE

(71) Applicant: DENSO CORPORATION, Kariya, Aichi-pref. (JP)

(72) Inventors: Takao Mishima, Kariya (JP); Mikiyasu Matsuoka, Kariya (JP); Shingo Nakata, Kariya (JP)

(73) Assignee: DENSO CORPORATION, Kariya (JP)

( * ) Notice: Subject to any disclaimer, the term of this patent is extended or adjusted under 35 U.S.C. 154(b) by 336 days.

(21) Appl. No.: 15/023,441

(22) PCT Filed: Sep. 25, 2014

(86) PCT No.: PCT/JP2014/004903
§ 371 (c)(1),
(2) Date: Mar. 21, 2016

(87) PCT Pub. No.: WO2015/045381
PCT Pub. Date: Apr. 2, 2015

(65) Prior Publication Data
US 2016/0230686 A1    Aug. 11, 2016

(30) Foreign Application Priority Data

Sep. 27, 2013 (JP) .................... 2013-202132
Sep. 17, 2014 (JP) .................... 2014-189033

(51) Int. Cl.
*G01N 27/407* (2006.01)
*F02D 41/14* (2006.01)
(Continued)

(52) U.S. Cl.
CPC ....... *F02D 41/1455* (2013.01); *F01N 13/008* (2013.01); *F02D 41/1454* (2013.01);
(Continued)

(58) Field of Classification Search
CPC .................................................. G01N 27/4065
See application file for complete search history.

(56) References Cited

U.S. PATENT DOCUMENTS 4,719,895 A    1/1988 Mieno et al.
4,762,604 A *  8/1988 Asakura ............. G01N 27/4065
                                              204/406
(Continued)

FOREIGN PATENT DOCUMENTS

JP    S60-78340         5/1985
JP    61-294355 A  * 12/1986    ............. G01N 27/58
(Continued)

OTHER PUBLICATIONS

Definition of "electrogenic" in the online Oxford Living Dicitonary, downloaded on May 2, 2018, from https://en.oxforddictionaries.com/definition/electrogenic (Year: 2018).*

(Continued)

*Primary Examiner* — Alexander S Noguerola
(74) *Attorney, Agent, or Firm* — Nixon & Vanderhye P.C.

(57) ABSTRACT

An $O_2$ sensor includes a sensor element using a solid electrolyte layer and a pair of electrodes placed at a position to interpose the solid electrolyte layer, detects an exhaust gas from an internal combustion engine as an object of a detection, and outputs an electromotive force signal depending on an air-fuel ratio of the exhaust gas. The sensor element is connected with a constant current circuit supplying a constant current that is prescribed. A microcomputer calculates a resistance value (element resistance) of the sensor element, and performs a restriction on the constant current supplied by the constant current circuit on the basis of the element resistance.

12 Claims, 11 Drawing Sheets

(51) Int. Cl.
    *G01N 27/409*     (2006.01)
    *F01N 13/00*     (2010.01)
    *G01N 27/406*     (2006.01)
    *G01N 27/416*     (2006.01)
    *G01N 27/417*     (2006.01)
    *F02D 41/06*     (2006.01)
    *F02D 41/12*     (2006.01)

(52) U.S. Cl.
    CPC ......... *G01N 27/407* (2013.01); *G01N 27/409* (2013.01); *G01N 27/4065* (2013.01); *G01N 27/4161* (2013.01); *G01N 27/4175* (2013.01); *F02D 41/064* (2013.01); *F02D 41/123* (2013.01); *F02D 41/1494* (2013.01)

(56) References Cited

U.S. PATENT DOCUMENTS

| | | |
|---|---|---|
| 2008/0277281 A1 | 11/2008 | Hiraiwa et al. |
| 2012/0043205 A1 | 2/2012 | Matsuoka et al. |

FOREIGN PATENT DOCUMENTS

| | | |
|---|---|---|
| JP | S62-76449 | 4/1987 |
| JP | S62-76451 | 4/1987 |

OTHER PUBLICATIONS

Definition of "electrogenic" in the online Oxford Reference—A Dictionary of Biology (6 ed.) downloaded May 2, 2018 from http://www.oxfordreference.com/view/10.1093/acref/9780199204625.001.0001/acref-9780199204625-e-6207 (Year: 2018).*
JPO English language abstract of Hasimoto et al. JP 61-294355 A, patented Dec. 25, 1986. (Year: 1986).*
Definition of "prescribe" in the online Merriam-Webster dictionary. Downloaded May 2, 2018 from https://www.merriam-webster.com/dictionary/prescribe (Year: 2018).*
Full English language translation of Hashimoto et al. JP 61-294355 A, patented Dec. 25, 1986 (Year: 1986).*
Full English language translation of Hashimoto et al. JP 62-76451 A, patented Sep. 30, 1985 (Year: 1985).*
Mishima et al., copending U.S. Appl. No. 15/023,446, filed Mar. 21, 2016.
Nakata et al., copending U.S. Appl. No. 15/023,435, filed Mar. 21, 2016.
International Search Report for PCT/JP2014/004903 dated Dec. 9, 2014, 5 pages.
Written Opinion of the ISA for PCT/JP2014/004903 dated Dec. 9, 2014, 8 pages.

* cited by examiner (a) 100μm     (b) 200μm     (c) 300μm

GAS SENSOR CONTROL DEVICE

CROSS REFERENCE TO RELATED APPLICATION

This application is the U.S. national phase of International Application No. PCT/JP2014/004903 filed on Sep. 25, 2014 which designated the U.S. and claims priority to Japanese Patent Application No. 2013-202132 filed on Sep. 27, 2013 and Japanese Patent Application No. 2014-189033 filed on Sep. 17, 2014, the entire contents of each of which are incorporated herein by reference.

TECHNICAL FIELD

The present disclosure relates to a gas sensor control device.

BACKGROUND ART

For example, a vehicle engine generally uses an electromotive force output type gas sensor which takes the exhaust gas discharged from the engine as an object of detection and detects the oxygen concentration. The gas sensor has an electrogenic cell which outputs an electromotive force signal which differs depending on whether the exhaust gas air-fuel ratio is rich or lean. Specifically, when the air-fuel ratio is rich, the gas sensor outputs an electromotive force signal of about 0.9 V and when the air-fuel ratio is lean, the gas sensor outputs an electromotive force signal of about 0 V.

As for this kind of gas sensor, attention has been drawn to the fact that when the air-fuel ratio of the exhaust gas changes to rich or lean, the sensor output changes with a delay from the actual change of the air-fuel ratio. Various techniques have been described to improve this output characteristic.

For example, in the gas sensor control device in Patent Literature 1, a constant current circuit is connected to at least one of a pair of sensor electrodes. When it is determined that a change request to change the output characteristic of the gas sensor has been generated, the direction of constant current is determined according to the change request and the constant current circuit is controlled so that the constant current flows in the determined direction. Thus, the output characteristic of the gas sensor is appropriately controlled by supplying the constant current.

In a gas sensor, the resistance value of the sensor element changes depending on the temperature of the sensor element. Specifically, when the engine is started in the cold or when the exhaust gas temperature decreases with fuel cut to the engine, the element resistance increases with the decrease in the temperature of the sensor element. In this case, as the element resistance increases, the voltage applied to the sensor element increases even under the condition that a constant current flows. When the applied voltage becomes excessive, a disadvantage (bad influence) such as deterioration of the solid electrolyte body of the sensor element may occur. Therefore, in the configuration in which a constant current is supplied to the sensor element, there is room for improvement from the viewpoint of protection of the sensor element. The sensor element corresponds to an electrogenic cell. The resistance value of the sensor element is also called the element resistance.

PRIOR ART LITERATURES

Patent Literature

Patent Literature 1: JP2012-63345A

SUMMARY OF INVENTION

The present disclosure has a main object to provide a gas sensor control device which performs air-fuel ratio detection properly while protecting the gas sensor.

According to the present disclosure, a gas sensor control device is applied to a gas sensor which has an electrogenic cell using a solid electrolyte body and a pair of electrodes placed at a position to interpose the solid electrolyte body, and detects an exhaust gas from an internal combustion engine as an object of a detection and outputs an electromotive force signal depending on an air-fuel ratio of the exhaust gas. The gas sensor control device includes a constant current supplying section supplying a constant current that is prescribed to the electrogenic cell, an influence determining section determining a possibility of an occurrence of a bad influence on the solid electrolyte body due to a supply of the constant current performed by the constant current supplying section, and a current control section that restricting the constant current supplied by the constant current supplying section when the influence determining section determines that the bad influence on the solid electrolyte body may occur.

When a constant current is supplied to the electrogenic cell, a bad influence on the solid electrolyte body may occur due to the supply of constant current. For example, when the engine is started in the cold or the exhaust gas temperature decreases with fuel cut to the engine, when the element resistance increases with the decrease in the sensor element temperature, the voltage applied to the sensor element may become excessive under the condition that the constant current flows, causing a disadvantage such as deterioration of the solid electrolyte body. In this respect, in the above configuration, when it is determined that a bad influence on the solid electrolyte body may occur, the constant current supplied by the constant current supplying section is restricted to suppress the possibility that an excessive voltage is applied on the sensor element. As a result, air-fuel ratio can be detected properly while the gas sensor is protected.

In addition, a resistance value calculating section which calculates the resistance value of the electrogenic cell may be provided so that the influence determining section determines the possibility of occurrence of a bad influence on the solid electrolyte body according to the resistance value of the electrogenic cell as calculated by the resistance value calculating section.

In the above structure, in expectation that the resistance value of the electrogenic cell will become large at the cold start of the internal combustion engine or with the decrease in the temperature of the electrogenic cell when the exhaust gas temperature decreases due to fuel cut to the internal combustion engine, the constant current supplied to the electrogenic cell is restricted according to the resistance value of the electrogenic cell. Consequently, even when the voltage applied to the electrogenic cell becomes high due to the increase in the resistance value of the electrogenic cell, the possibility of a disadvantage attributable to application of excessive voltage (such as a deterioration of the solid electrolyte body) can be suppressed. As a result, the air-fuel ratio can be detected appropriately while the gas sensor is protected.

BRIEF DESCRIPTION OF DRAWINGS

The above and other objects, features and advantages of the present disclosure will become more apparent from the following detailed description made with reference to the accompanying drawings. In the drawings.

DESCRIPTION OF EMBODIMENTS (First Embodiment)

Figure 1:
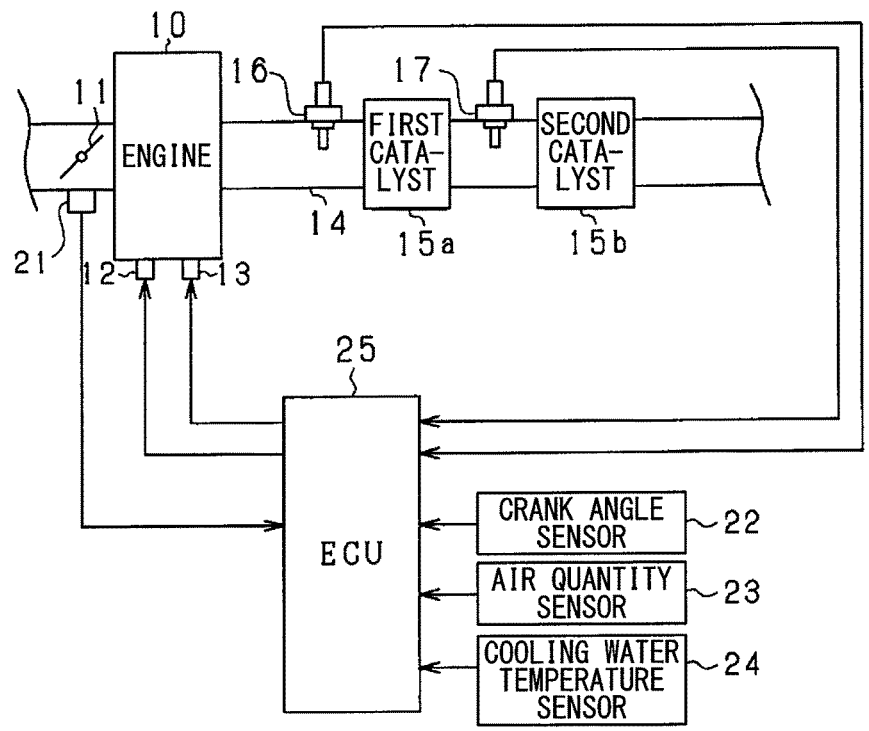
FIG. 1 is a schematic diagram which shows the general configuration of an engine control system.

Next, an embodiment of a gas sensor control device according to the present disclosure will be described referring to drawings. This embodiment concerns an engine control system which uses a gas sensor located on the exhaust pipe of an on-vehicle engine (internal combustion engine) to perform various controls, etc. of the engine according to output of the gas sensor. The control system, centered on an electronic control unit (ECU), performs control of the amount of fuel injection, control of ignition timing and so on. FIG. 1 is a block diagram which shows the general configuration of the system.

In FIG. 1, an engine 10 is, for example, a gasoline engine which includes a throttle valve 11 that is electronically controlled, a fuel injection valve 12, and an ignition device 13. An exhaust pipe 14 of the engine 10 is provided with catalysts 15a and 15b as exhaust gas purifying devices. The exhaust pipe 14 corresponds to an exhaust section. The catalysts 15a and 15b are, for example, both three-way catalysts; the catalyst 15a is a first catalyst as an upstream catalyst and the catalyst 15b is a second catalyst as a downstream catalyst. As widely known, a three-way catalyst purifies three major emission toxic components, carbon monoxide (CO), hydrocarbon (HC), and nitrogen oxide (NOx) such as NO, and is structured so that metal such as platinum, palladium, or rhodium is supported by a honeycomb or lattice-shaped ceramic support. In this case, the three-way catalyst purifies CO and HC as rich components by oxidation action and NOx as a lean component by reduction action.

An A/F sensor 16 is located upstream of the first catalyst 15a and an $O_2$ sensor 17 is located between the catalysts 15a and 15b (downstream of the first catalyst 15a and upstream of the second catalyst 15b). The A/F sensor 16 outputs an A/F signal which is roughly proportional to the air-fuel ratio of the exhaust gas. The $O_2$ sensor 17 also outputs an electromotive force signal which differs depending on whether the air-fuel ratio of the exhaust gas is lean or rich.

The system further includes various sensors including a throttle opening sensor 21 which detects the opening of the throttle valve 11, a crank angle sensor 22 which outputs a rectangular crank angle signal at every prescribed crank angle of the engine, an air quantity sensor 23 which detects the quantity of intake air in the engine 10, and a cooling water temperature sensor 24 which detects the temperature of engine cooling water. In addition to the above, the system includes a combustion pressure sensor which detects the combustion pressure in the cylinder, an accelerator opening sensor which detects the opening of the accelerator (amount of operation of the accelerator), and an oil temperature sensor which detects the temperature of engine lubricant, though not shown in the figure. In this embodiment, the prescribed crank angle is 30° CA cycle. These sensors correspond to an operation condition detecting section.

An ECU 25 is mainly comprised of a known microcomputer 41 which includes a CPU, ROM, and RAM, and executes various control programs stored in the ROM to perform various controls of the engine 10 depending on each engine operation condition. In other words, the ECU 25 receives signals from the above various sensors, etc. and calculates the amount of fuel injection and ignition timing according to the various signals to control the drive of the fuel injection valve 12 and the ignition device 13.

In connection with the amount control of fuel injection, the ECU 25 performs air-fuel ratio feedback control according to a detection signal from the A/F sensor 16 on the upstream of the first catalyst and a detection signal from the $O_2$ sensor 17 on the downstream of the first catalyst. Specifically, the ECU 25 performs main feedback control so that the actual air-fuel ratio (actual air-fuel ratio on the catalyst upstream side) detected by the A/F sensor 16 becomes a target air-fuel ratio set according to the engine operation condition, and also performs sub-feedback control so that the actual air-fuel ratio (actual air-fuel ratio on the catalyst downstream side) detected by the $O_2$ sensor 17 becomes the target air-fuel ratio. In sub-feedback control, for example, according to the difference between the actual air-fuel ratio on the catalyst downstream side and the target air-fuel ratio, the target air fuel ratio in main feedback control is modified or the amount of feedback correction in the main feedback control is modified. For air-fuel ratio control, for example, the ECU 25 performs stoichiometric feedback to make the target air-fuel ratio stoichiometric or nearly stoichiometric. In this case, stoichiometry is equivalent to a theoretical air-fuel ratio.

Figure 2:
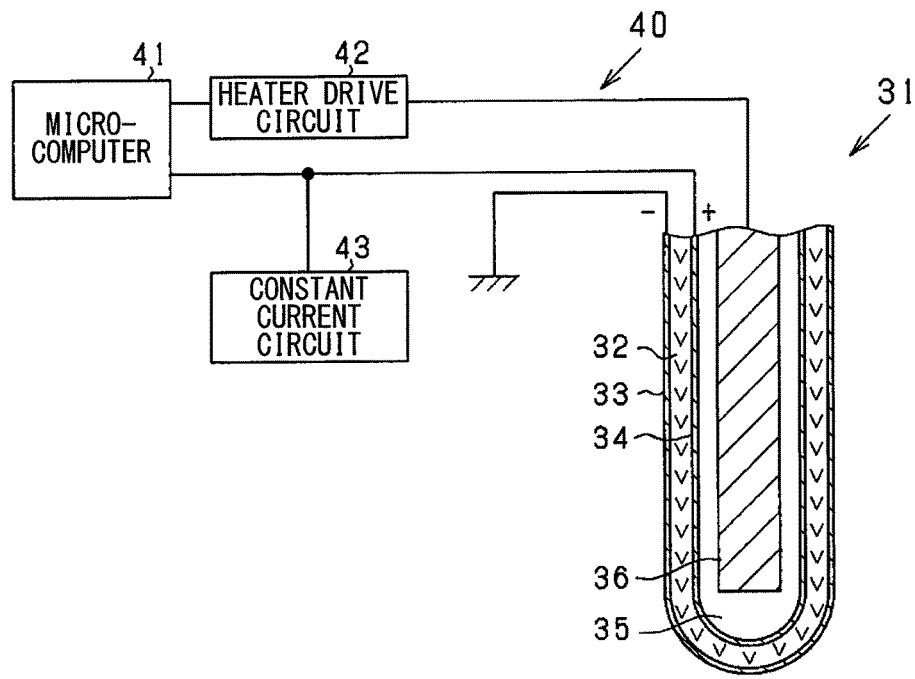
FIG. 2 is a diagram which shows the cross-sectional structure of a sensor element and the general structure of a sensor control section.

Next, the structure of the $O_2$ sensor 17 on the downstream of the first catalyst will be described. The $O_2$ sensor 17 has a sensor element 31 with a cup-shaped structure. FIG. 2 shows the cross-sectional structure of the sensor element 31. Specifically, the sensor element 31 has a roughly U-shaped cross section. Actually, the sensor element 31 is entirely housed in a housing or element cover and installed in the engine exhaust pipe. The sensor element 31 corresponds to an electrogenic cell.

The sensor element 31 has a solid electrolyte layer 32 with a roughly U-shaped cross section and an exhaust side electrode 33 on its outer surface and an air side electrode 34 on its inner surface. These electrodes 33 and 34 lie as layers on the surfaces of the solid electrolyte layer 32. The solid electrolyte layer 32 has an oxygen ion-conductive sintered oxide made by dissolving CaO, MgO, $Y_2O_3$, $Yb_2O_3$ or the like as a stabilizer in $ZrO_2$, $HfO_2$, $ThO_2$, $Bi_2O_3$ or the like. The electrodes 33 and 34 are both made of a catalytically active precious metal such as platinum and have a porous chemical coating or the like on their surfaces. The electrodes 33 and 34 are a pair of opposite electrodes and also called sensor electrodes. The inner space surrounded by the solid electrolyte layer 32 is an air chamber 35 in which an atmospheric air as reference gas is introduced and a heater 36 is housed in the air chamber 35. The air chamber 35 is also called the reference chamber. The heater 36 has a sufficient heat generating capacity to activate the sensor element 31 and heats the entire sensor element with its generated heat energy. The activation temperature of the $O_2$ sensor 17 is, for example, about 500 to 650° C. The inside of the air chamber 35 is maintained at a prescribed oxygen concentration by introduction of the air.

In the above sensor element 31, the outer side of the solid electrolyte layer 32 which is near the exhaust side electrode 33 has an exhaust gas atmosphere and the inner side of the solid electrolyte layer 32 which is near the air side electrode 34 has an air atmosphere, and depending on the oxygen concentration difference (oxygen partial pressure difference) between them, an electromotive force is generated between the electrodes 33 and 34. In short, an electromotive force which differs depending on whether the air-fuel ratio is rich or lean is generated. In this case, the exhaust side electrode 33 is lower in oxygen concentration than the air side electrode 34 as the reference electrode and in the sensor element 31, an electromotive force is generated with the air side electrode 34 as the positive side and the exhaust side electrode 33 as the negative side. Consequently, the $O_2$ sensor 17 outputs an electromotive force signal which depends on the oxygen concentration of the exhaust gas (namely, air-fuel ratio).

Figure 3:
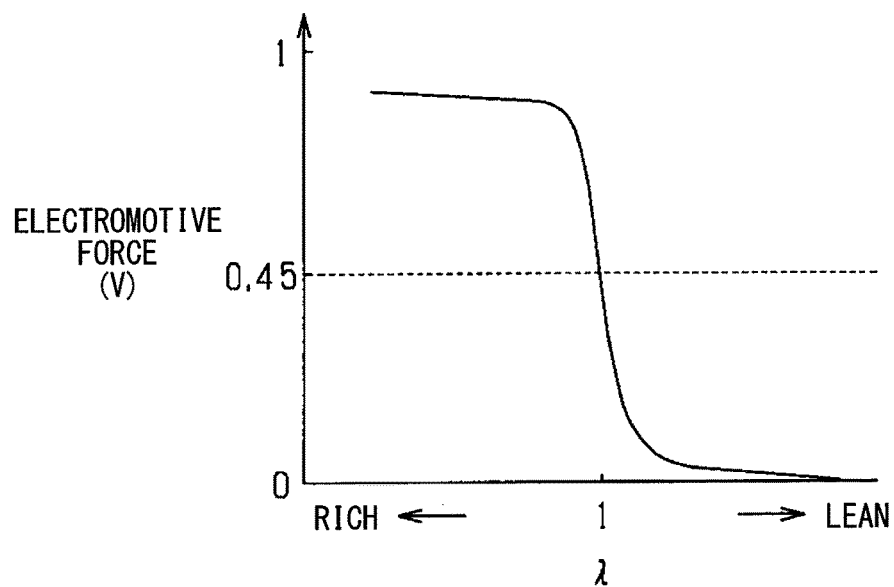
FIG. 3 is an electromotive force characteristic graph which shows the relation between excess air ratio and the electromotive force of the sensor element.

FIG. 3 is an electromotive force characteristic graph which shows the relation between excess air ratio λ of the exhaust gas and the electromotive force of the sensor element 31. In FIG. 3, the horizontal axis represents excess air ratio λ and when λ is 1, the air-fuel ratio of the exhaust gas is stoichiometric. The sensor element 31 generates an electromotive force which differs depending on whether the air-fuel ratio is rich or lean, and has a characteristic that the electromotive force suddenly changes when the ratio is nearly stoichiometric. Specifically, when the ratio is rich, the electromotive force of the sensor element 31 is about 0.9 V and when the ratio is lean, the electromotive force of the sensor element 31 is about 0 V.

In FIG. 2, a sensor control section 40 is connected to the sensor element 31 and when an electromotive force is generated in the sensor element 31 depending on the air-fuel ratio (oxygen concentration) of the exhaust gas, a sensor detection signal (electromotive force signal) equivalent to the electromotive force is sent to a microcomputer 41 in the sensor control section 40. The microcomputer 41 calculates the air-fuel ratio according to the electromotive force signal from the sensor element 31. The sensor control section 40 is located in the ECU 25 shown in FIG. 1. In the ECU 25, the microcomputer 41 is provided as a calculating section which has an engine control function and a sensor control function. In this case, the microcomputer 41 calculates the engine rotation speed and the intake air amount according to the results of detection by the above various sensors. Alternatively, in the ECU 25, a microcomputer for engine control and a microcomputer for sensor control may be provided separately.

The microcomputer 41 makes a determination about the activity state of the sensor element 31 and also controls the heater 36 through a heater drive circuit 42 according to the result of the determination.

Furthermore, in this embodiment, in order to change the output characteristic (electromotive force characteristic) of the $O_2$ sensor 17, a prescribed constant current is supplied to between the pair of electrodes 33 and 34 in the sensor element 31. In other words, the sensor element 31 performs oxygen pumping. The sensor element 31 increases the exhaust emission reduction effect in air-fuel ratio feedback control by changing the output characteristic. The principle on which the sensor output characteristic is changed by supplying a constant current is as follows.

Figure 4:
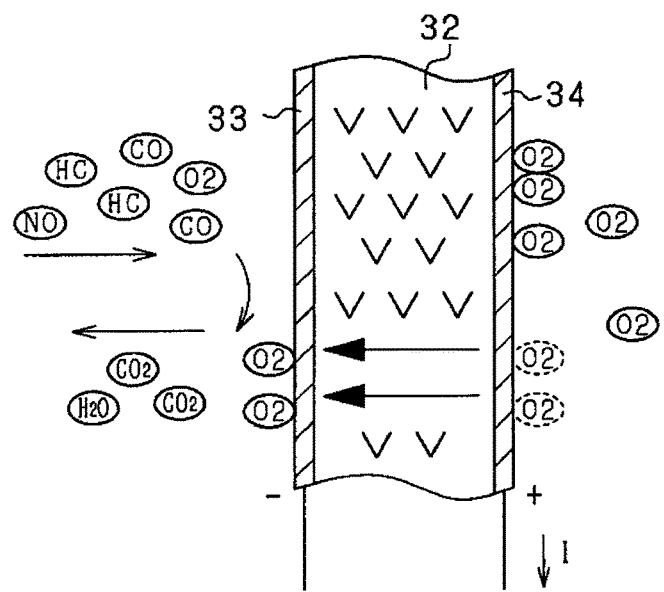
FIG. 4 is a schematic diagram which shows the reaction of gas components in the sensor element.
Figure 5:
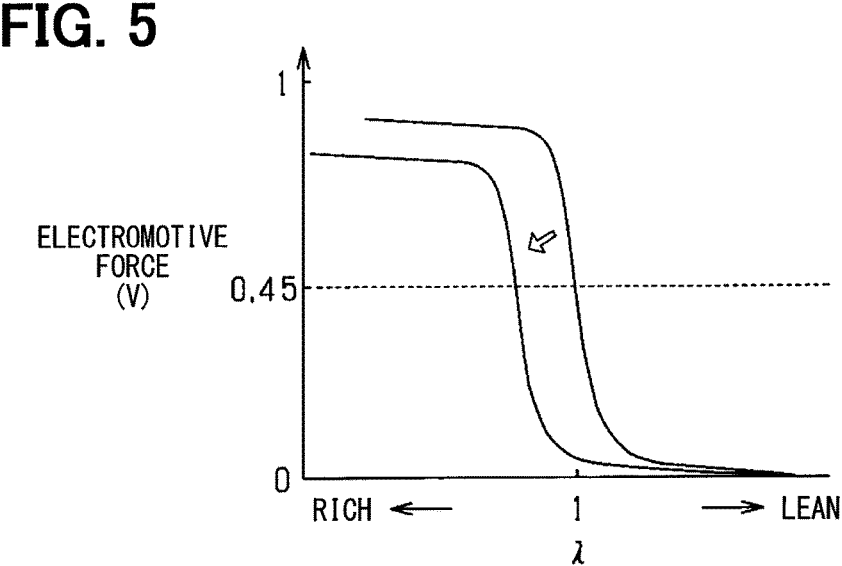
FIG. 5 is an electromotive force characteristic graph which shows the relation between excess air ratio and the electromotive force of the sensor element.

As shown in FIG. 4, there are CO, HC, $NO_x$, and $O_2$ in the vicinity of the exhaust side electrode 33 of the $O_2$ sensor 17 and in this condition, a current is supplied to the sensor element 31 so that oxygen ions move from the air side electrode 34 to the exhaust side electrode 33 through the solid electrolyte layer 32. Specifically, oxygen pumping is performed in the sensor element 31. In this case, at the exhaust side electrode 33, the oxygens which have moved to the exhaust side electrode 33 through the solid electrolyte layer 32 react with CO and HC and generate $CO_2$ and $H_2O$. Consequently, CO and HC are removed in the vicinity of the exhaust side electrode 33 and the equilibrium point of gas reaction in the vicinity of the exhaust side electrode 33 of the $O_2$ sensor 17 shifts to the rich side. In other words, as shown in FIG. 5, the sensor output characteristic which indicates the relation between excess air ratio λ and electromotive force as a whole shifts to the rich side and accordingly, the point at which the electromotive force becomes the stoichiometric value (0.45 V) shifts to the rich side.

Next, the structure of the sensor control section 40 which performs control for the $O_2$ sensor 17 will be described. The structure of the sensor control section 40 is as illustrated in FIG. 2 and the sensor control section 40 has the microcomputer 41 as a control section. The microcomputer 41 receives an electromotive force signal from the sensor element 31 through an A/D converter, etc. and calculates the air-fuel ratio of the exhaust gas according to the electromotive force signal. Alternatively, the microcomputer 41 calculates the air-fuel ratio on the catalyst downstream according to the electromotive force signal. A constant current circuit 43 as a constant current supplying section is connected midway in an electric pathway which electrically connects the air side electrode 34 of the sensor element 31 and the microcomputer 41. When the sensor element 31 generates an electromotive force, the constant current circuit 43 receives the electromotive force from the sensor element 31 and supplies a current, which depends on the electromotive force, to the sensor element 31. In this case, according to the constant current circuit 43, the current flows from the exhaust side electrode 33 to the air side electrode 34 through the solid electrolyte layer 32 and accordingly oxygen ions move in the solid electrolyte layer 32 from the air side electrode 34 to the exhaust side electrode 33.

The structure of the constant current circuit 43 of the sensor control section 40 and the peripheral circuit around the circuit 43 will be described in more detail referring to FIG. 6.

Figure 6:
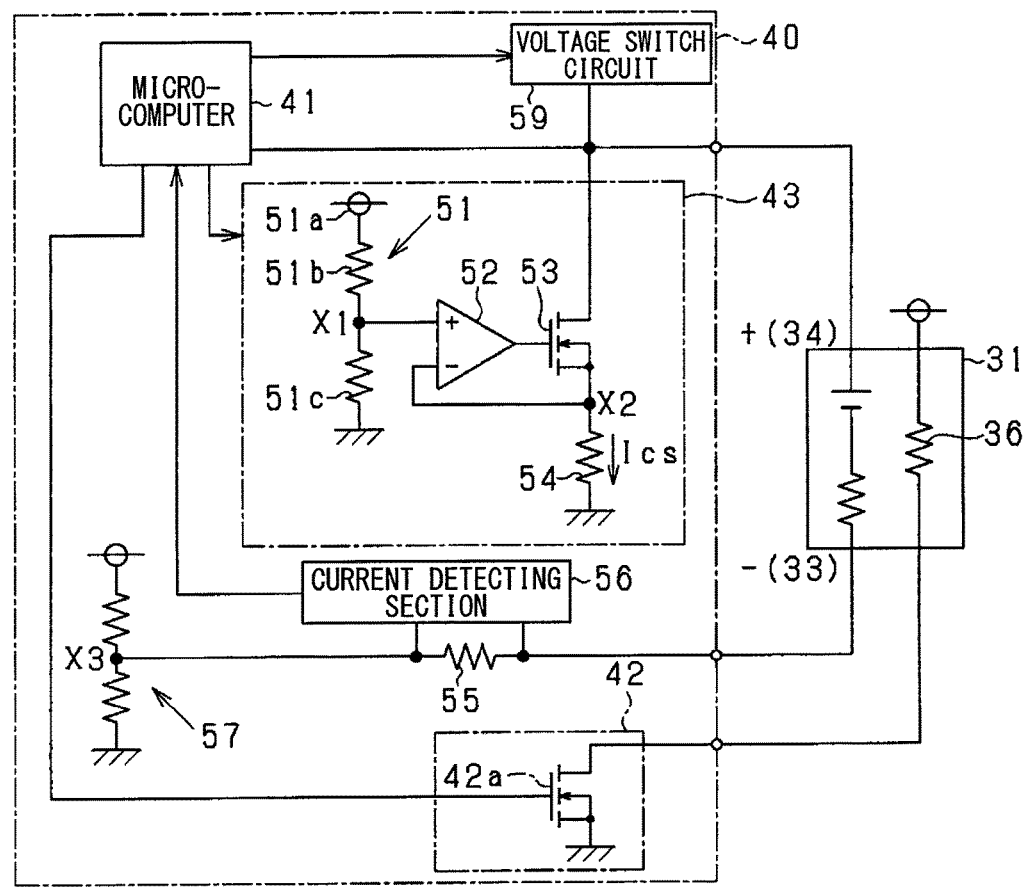
FIG. 6 is a diagram which shows the structure of the sensor control section.

In FIG. 6, the constant current circuit 43 includes a voltage generating section 51 to generate a prescribed constant voltage, an operational amplifier 52, an n-channel MOSFET 53 to be driven by output of the operational amplifier 52, and a resistance 54 connected to the source of the MOSFET 53. In the voltage generating section 51, a constant voltage source 51*a* and resistances 51*b* and 51*c* are connected in series and the middle point between the resistances 51*b* and 51*c* is voltage output point X1. In this embodiment, the constant voltage source 51*a* is 5 V. In the operational amplifier 52, the + input terminal is connected to voltage output point X1 and the output terminal is connected to the gate of the MOSFET 53. Also, the − input terminal is connected to middle point X2 between the MOSFET 53 and the resistance 54. From the viewpoint of the MOSFET 53, the gate is connected to the output terminal of the operational amplifier 52, the drain is connected to the air side electrode 34 of the sensor element 31 and the source is connected to the resistance 54.

The above constant current circuit 43 operates so that the voltage of the + input terminal of the operational amplifier 52 is equal to the voltage of its − input terminal, so the voltage at X2 becomes equal to the voltage at X1. Then, constant current Ics, the amount of which is determined by the voltage at X2 and the resistance value of the resistance 54, flows in the series circuit including the sensor element 31, MOSFET 53, and resistance 54. At this time, the MOSFET 53 operates according to the operational amplifier output voltage based on the difference between + and − input voltages and functions as a current control element which supplies a constant current Ics.

Here, the voltage at X1 and X2 and the resistance value of the resistance 54 should be determined according to the amount of current which is required to flow in the sensor element 31 when an electromotive force is generated in the sensor element 31. Specifically, when an electromotive force (0 to 0.9 V) is generated in the sensor element 31, when a current of 0.1 mA is to flow in the sensor element 31, for example, the voltage at X1 and X2 should be 10 mV and the resistance value of the resistance 54 should be 100Ω. When a current of 0.2 mA is to flow, for example, the voltage at X1 and X2 should be 20 mV and the resistance value of the resistance 54 should be 100Ω. When the current amount range is to be 0.1 to 2.0 mA, when the resistance value of the resistance 54 is 100Ω, the voltage at X1 and X2 should be in the rage of 10 mV to 200 mV.

In the sensor control section 40 which uses the above constant current circuit 43, when an electromotive force is generated in the sensor element 31, the prescribed constant current Ics flows in the MOSFET 53 and resistance 54 with the electromotive force as a power source (namely, the sensor element 31 functions as a battery). The output characteristic of the $O_2$ sensor 17 can be thus changed.

In this embodiment, the constant current Ics supplied by the constant current circuit 43 can be changed according to a command from the microcomputer 41 and the constant current Ics can be increased or decreased according to each condition. Specifically, the voltage value at points X1 and X2 are changed, for example, by changing the resistance ratio between the resistances 51*b* and 51*c* according to a command from the microcomputer 41 and accordingly the constant current Ics is changed.

The first end of a shunt resistance 55 for current detection is connected to the exhaust side electrode 33 of the sensor element 31 and the second end of the shunt resistance 55 is connected to a voltage circuit 57. The current which flows in the shunt resistance 55 is detected by a current detecting section 56 and the detection signals are sent to the microcomputer 41 sequentially. The current detecting section 56 may be a differential amplifier circuit which uses, for example, an operational amplifier or the like. In FIG. 2, in the sensor control section 40, components such as the shunt resistance 55 and voltage circuit 57 (other components than the constant current circuit 43 and heater drive circuit 42) are omitted.

The voltage circuit 57, which is intended to apply a positive voltage to the exhaust side electrode 33, is an offset voltage circuit which makes the potential of the exhaust side electrode 33 higher by a given potential than the potential on the side from which a current flows in the constant current circuit 43 (grounding side potential of the resistance 54). The voltage circuit 57 has a voltage dividing circuit which generates a prescribed offset voltage and the middle point of the voltage dividing circuit is offset voltage point X3. The voltage at the offset voltage point X3 is, for example, 2.0 V.

A voltage switch circuit 59 is connected to the air side electrode 34 of the sensor element 31. This voltage switch circuit 59 temporarily sweeps the voltage applied to the sensor element 31 according to a command from the microcomputer 41 and the resistance value of the sensor element 31 can be detected by the current detecting section 56 detecting the amount of current change with the voltage change. The resistance value of the sensor element 31 is also called the element resistance. The element resistance is detected in a given cycle and during the detection, the sensor applied voltage is changed by sweeping. When the applied voltage is changed by sweeping, the sensor applied voltage may be changed toward the positive side or toward both the positive and negative sides. In calculation of the element resistance, instead of changing the voltage by sweeping, the current may be changed by sweeping so that the element resistance is calculated from the amount of the resulting voltage change.

Furthermore, in the sensor control section 40, the heater drive circuit 42 has a switching element 42*a* which turns on/off the power to the heater 36. In the sensor element 31, heater energization is controlled by turning on/off the switching element 42*a*, so that the sensor element 31 is maintained in a prescribed active state. In this prescribed active state, the activation temperature is 500 to 650° C. The control of heater energization by the microcomputer 41 is briefly outlined below. Before activation of the sensor element 31, in order to expedite activation, the switching element 42*a* is kept ON and the heater 36 is heated with the maximum electric power. In this case, energization control is wholly performed. After activation of the sensor element 31, the amount of heater energization is feedback-controlled according to the difference between the target value and the actual value (calculated value) of the element resistance. For example, the amount of duty control at each time is calculated by the PID control method and energization of the heater is performed by turning on/off the switching element 42a according to the amount of duty control.

Since the resistance value of the sensor element 31 changes depending on the temperature of the sensor element 31, when the engine 10 is started in the cold or when the exhaust gas temperature decreases with fuel cut to the engine 10, the element resistance increases as the temperature of the sensor element 31 decreases. In this case, as the element resistance increases, the voltage applied to the sensor element 31 (=element resistance x constant current Ics) increases even under the condition that a prescribed constant current Ics flows. When the applied voltage becomes excessive, a disadvantage (bad influence) such as deterioration of the solid electrolyte layer 32 may occur in the sensor element 31. The temperature of the sensor element 31 is also called the element temperature.

It is known that reduction reaction occurs in $ZrO_2$ upon application of 2.24 V and reduction reaction occurs in $Y_2O_3$ upon application of 2.75 V. As reduction reaction occurs, $ZrO_2$ or $Y_2O_3$ deteriorates, which may change the electrolyte property and in the worst case, damage the solid electrolyte layer. In the process of manufacturing the $O_2$ sensor 17, it may happen that the solid electrolyte layer 32 contains an impurity and the voltage which reduces $ZrO_2$ or $Y_2O_3$ decreases depending on the type of the impurity. Even when an ingredient other than the main ingredient deteriorates in the solid electrolyte layer 32, the same kind of disadvantage occurs as when a defect occurs in the solid electrolyte layer 32. Therefore, attention must be paid to voltage change.

Figure 7:
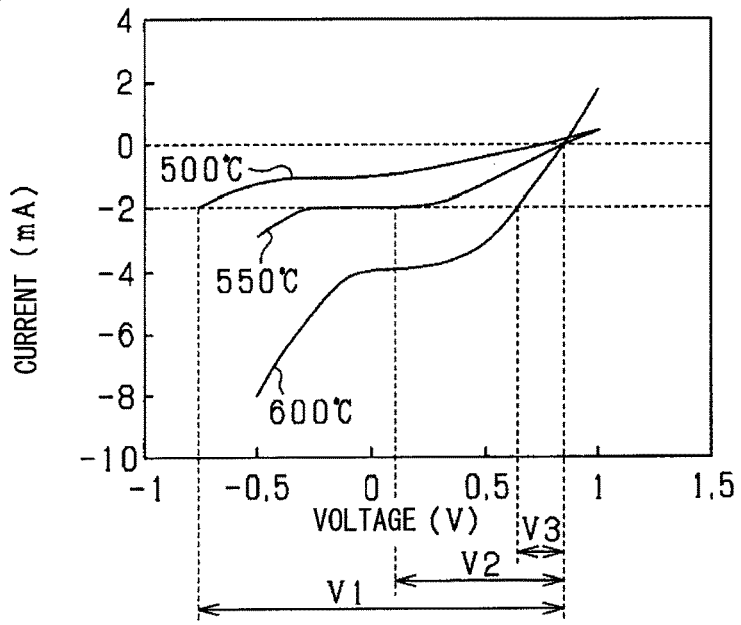
FIG. 7 is a graph which shows the relation between current and the amount of voltage drop when a constant current flows.

Next, the relation between current and the amount of voltage drop under the condition that the constant current Ics flows in the sensor element 31 will be explained referring to FIG. 7. FIG. 7 shows the relation between current and the amount of voltage drop when the element temperature is 500° C., 550° C., and 600° C. According to FIG. 7, for example, constant current of 2 mA is supplied and the minus symbol in the figure denotes the direction of current. When the element temperature is 500° C., the element resistance is 800Ω and voltage drop of about 1.6 V occurs as indicated by V1. When the element temperature is 550° C., the element resistance is 300Ω and voltage drop of about 0.6 V occurs as indicated by V2. When the element temperature is 600° C., the element resistance is 100Ω and voltage drop of about 0.2 V occurs as indicated by V3. In short, when the sensor element 31 has a lower temperature, the amount of voltage drop is larger.

For example, assuming that the allowable amount of voltage drop is 1.5 V, when constant current of 2 mA is supplied, when the element temperature is 500° C., the amount of voltage drop (1.6V) at that time is not allowable; when the element temperature is 550° C. or 600° C., the amount of voltage drop (0.6 V or 0.2 V) at that time is allowable.

Therefore, in this embodiment, the possibility of occurrence of a bad influence on the solid electrolyte layer 32 is determined according to the resistance value of the sensor element 31 and the constant current Ics supplied to the sensor element 31 is restricted according to the result of the determination. Consequently the possibility that the voltage applied to the sensor element 31 becomes excessive is suppressed and the sensor element 31 is protected.

Figure 8:
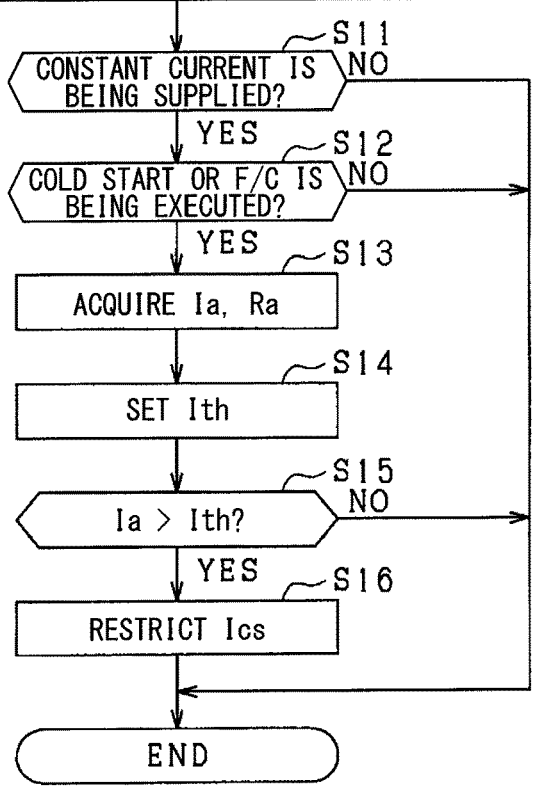
FIG. 8 is a flowchart which shows the constant current control process in a first embodiment.

FIG. 8 is a flowchart which shows the constant current control process and this process is repeated by the microcomputer 41 in a given cycle.

In FIG. 8, at S11 the microcomputer 41 determines whether or not the constant current is being supplied by the constant current circuit 43. At S12, the microcomputer 41 determines whether or not cold start of the engine 10 or fuel cut is being executed. When NO at S11 or S12, the microcomputer 41 ends this process or when YES at both S11 and S12, and then proceeds to the next step S13. In this embodiment, the step S12 corresponds to a condition determining section.

Figure 9:
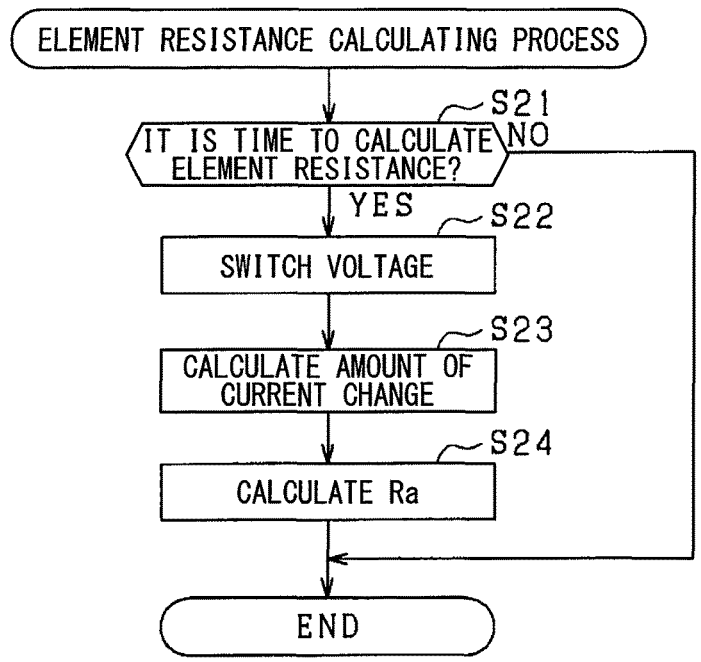
FIG. 9 is a flowchart which shows the element resistance calculating process.

At S13, the microcomputer 41 acquires actual current Ia and element resistance Ra. The actual current Ia is the current value detected by the current detecting section 56 in FIG. 6 and is equivalent to the constant current Ics which flows in the sensor element 31. The element resistance Ra should be calculated by the microcomputer 41 in a given cycle; for example, the element resistance Ra is calculated through the process shown in FIG. 9. In FIG. 9, at S21 the microcomputer 41 determines whether or not it is time to calculate the element resistance. When the microcomputer 41 determines that it is time to calculate, the microcomputer 41 proceeds to S22. The element resistance calculation interval is, for example, 128 msec. At S22, the microcomputer 41 temporarily switches the sensor applied voltage through the voltage switch circuit 59. At S23, the microcomputer 41 calculates the amount of current change which occurs depending on the voltage change. Furthermore, at S24 the microcomputer 41 calculates element resistance Ra from the amount of current change calculated at S23. In this embodiment, the step S24 corresponds to a resistance value calculating section.

Figure 10:
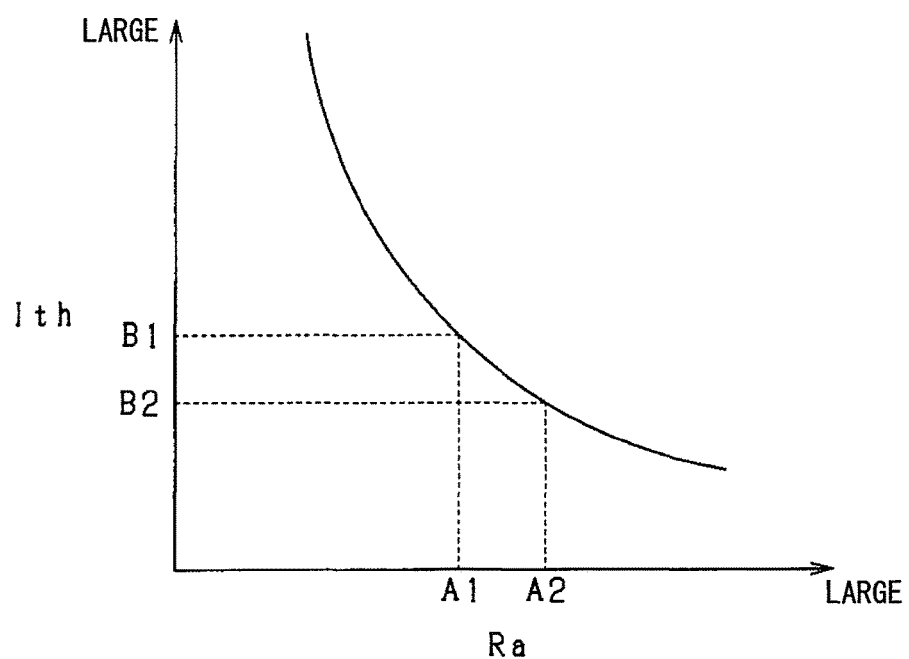
FIG. 10 is a graph which shows the relation between element resistance and allowable current value.

At S14, the microcomputer 41 sets the upper limit of current allowed to flow in the sensor element 31 as an allowable current value Ith, according to the element resistance Ra. At this time, the allowable current value Ith is set, for example, using the relation in FIG. 10. According to FIG. 10, when the element resistance value Ra is larger, a smaller value is set as the allowable current value Ith. More specifically, assuming that A1 represents the element resistance corresponding to the reference temperature (for example, 600° C.) of the sensor element 31, when the element temperature is lower than the reference temperature, the element resistance is A2 which is larger than A1. In this case, when the element resistance is larger, the amount of voltage change of the sensor element 31 is larger under the condition that a prescribed constant current is supplied, so "B2" as the allowable current value Ith at element resistance A2 is set as a smaller value than "B1" as the allowable current value Ith at element resistance A1. In this embodiment, the step S14 corresponds to an influence determining section and an allowable value setting section.

After that, at S15 the microcomputer 41 compares the actual current Ia and the allowable current value Ith and determines whether Ia>Ith or not. When Ia≤Ith, the microcomputer 41 determines that the ongoing constant current supply by the constant current circuit 43 is allowable, and ends this process. When Ia>Ith, the microcomputer 41 proceeds to S16 and restricts the ongoing constant current supply for the reason that a bad influence on the solid electrolyte layer 32 may occur. At this time, the microcomputer 41 decreases the constant current Ics so as to make the constant current Ics supplied by the constant current circuit 43 be not more than the allowable current value Ith. In this embodiment, the step S15 corresponds to an influence determining section and a current determining section and the step S16 corresponds to a current control section.

When Ia>Ith, the microcomputer 41 calculates the amount of current decrease ΔI from the excess of the actual current Ia (or constant current Ics) over the allowable current value Ith. For example, assuming that ΔI=(Ia (or Ics))−Ith) or that ΔI=Ia (or Ics)−Ith/n (n>1), the microcomputer 41 decreases the constant current Ics by the amount of current decrease ΔI (Ics=Ics−ΔI).

Figure 11:
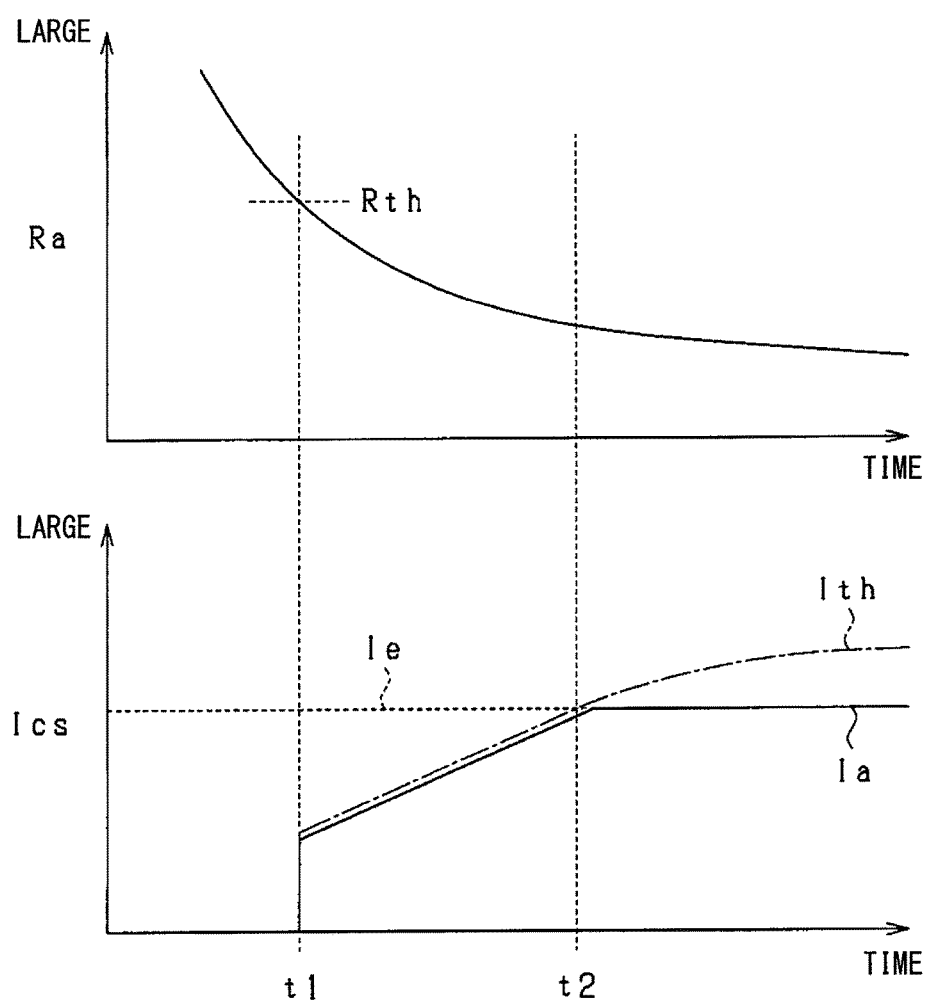
FIG. 11 is a time chart which shows constant current control at the time of engine start.

FIG. 11 is a time chart which shows constant current control at the start of the engine. FIG. 11 shows that in this embodiment, when the engine 10 is started in the cold, the temperature of the sensor element 31 rises gradually. In this case, the element resistance Ra decreases with time. In this embodiment, the reference value Ie of constant current is determined and under the condition that there is no restriction on current, the constant current circuit 43 supplies constant current Ie. In FIG. 11, the actual current Ia is expressed by solid line and the allowable current value Ith is expressed by dashed-dotted line.

In FIG. 11, before timing t1, the element resistance Ra drops from the maximum value. At timing t1, the element resistance Ra reaches a prescribed threshold Rth (for example, 1000Ω), which starts the supply of constant current by the constant current circuit 43. In this embodiment, the prescribed threshold Rth is 1000Ω. After the timing t1, the allowable current value Ith is set according to the element resistance Ra and the constant current is restricted by the allowable current value Ith. Just after the timing t1, the actual current Ia (constant current Ics) is below the allowable current value Ith and the constant current is restricted by the allowable current value Ith.

After that, the element resistance Ra decreases with the rise in the temperature of the sensor element 31 and the allowable current value Ith gradually increases with the decrease in the element resistance Ra. Then, at timing t2, the relation of Ia≤Ith is established and after that, the constant current is supplied to the sensor element 31 without restriction.

In the period from timing t1 to t2, which is just after start of the engine, the sensor element 31 has a low temperature and the element resistance is relatively large. When a prescribed constant current is supplied under such condition, an excessive voltage would be applied to the sensor element 31 and accordingly a disadvantage such as deterioration of the solid electrolyte layer 32 in the sensor element 31 might occur. Since the constant current is restricted as mentioned above, the possibility of occurrence of a disadvantage is suppressed.

Even after the sensor element 31 becomes active, the element temperature may decrease, for example, during fuel cut after completion of warming up or when the engine is stopped under idling stop control, leading to the risk of an excessive voltage being applied to the sensor element 31, though an explanation with reference to drawings is omitted. In this respect as well, the above restriction on constant current suppresses occurrence of a disadvantage.

According to the embodiment detailed above, the following advantageous effects will be brought about.

In the above structure, in expectation that the element resistance will become large at the cold start of the engine 10 or with the decrease in the temperature of the sensor element 31 when the exhaust gas temperature decreases due to fuel cut to the engine 10, the constant current supplied to the sensor element 31 is restricted according to the element resistance. Consequently, even when the voltage applied to the sensor element 31 becomes high due to the increase in the element resistance, the possibility of a disadvantage attributable to application of excessive voltage, for example, deterioration of the solid electrolyte layer 32, can be suppressed. As a result, the air-fuel ratio can be detected appropriately while the $O_2$ sensor 17 is protected.

The upper limit of current which can be supplied to the sensor element 31 is set as the allowable current value Ith according to the element resistance and the supply of constant current is restricted when the constant current (actual current Ia) of the sensor element 31 reaches the allowable current value Ith, so the constant current can be supplied appropriately according to the relation between the constant current and the allowable current value Ith.

When the constant current (actual current Ia) which flows in the sensor element 31 exceeds the allowable current value Ith, the constant current is decreased according to the amount of current decrease as calculated from the amount of excess of the constant current. Consequently, the amount of decrease of the constant current can be adjusted appropriately and even when the element resistance increases due to the decrease in the temperature of the sensor element 31, current restriction can be appropriately performed accordingly.

The sensor element 31 has a relatively low temperature at the cold start of the engine 10 or during fuel cut. Under such a low-temperature condition, a disadvantage attributable to application of an excessive voltage, such as deterioration of the solid electrolyte body may occur. In this respect, when it is determined that cold start or fuel cut is being executed, the supply of constant current is restricted and thus a condition in which a disadvantage is likely to occur can be addressed appropriately.

(Modification of the First Embodiment)

In the above embodiment, the actual current Ia which flows in the sensor element 31 is calculated and the constant current is restricted on the basis of comparison between the actual current Ia and the allowable current value Ith; however, this may be altered. For example, the constant current may be restricted on the basis of comparison between the constant current supplied by the constant current circuit 43 (current value specified by the microcomputer 41, for example, reference value Ie) and the allowable current value Ith.

In the above embodiment, as restriction on the supply of constant current, when the constant current reaches the allowable current value Ith as an allowable value, the constant current is restricted by the allowable current value Ith; however, this may be altered to an arrangement that the supply of constant current is stopped when the constant current reaches the allowable current value Ith. The following is an example related to the cold start of the engine 10: when the element resistance gradually increases as warming up progresses after engine start, the supply of constant current is stopped until the allowable current value Ith calculated from the element resistance exceeds the constant current reference value Ie.

The constant current Ics to be supplied by the constant current circuit 43 may be set as a variable according to the engine operation condition, etc. When the engine operation condition changes, the amount of rich components in the exhaust gas changes accordingly. Specifically, when the engine rotation speed is higher or the engine load is larger, the amount of rich components in the exhaust gas increases. In this case, in order to maintain the desired performance concerning the exhaust emission, it is desirable to control the constant current Ics of the constant current circuit 43 as the current to be supplied to the sensor element 31 as a variable according to the engine operation condition. For example, when the engine rotation speed is higher or the engine load is larger, the constant current Ics should be increased.

Although in the above embodiment, the $O_2$ sensor 17 is located downstream of the first catalyst 15a, instead the $O_2$ sensor 17 may be located in the middle portion of the first catalyst 15a. In this case, the $O_2$ sensor 17 may be located on the support of the first catalyst 15a. In any case, the $O_2$ sensor 17 should at least take the exhaust gas purified by the first catalyst 15a as the object of detection and detect the gas components.

Next, another embodiment which is different from the above first embodiment will be described with focus on the differences from the first embodiment.

(Second Embodiment)

Figure 12:
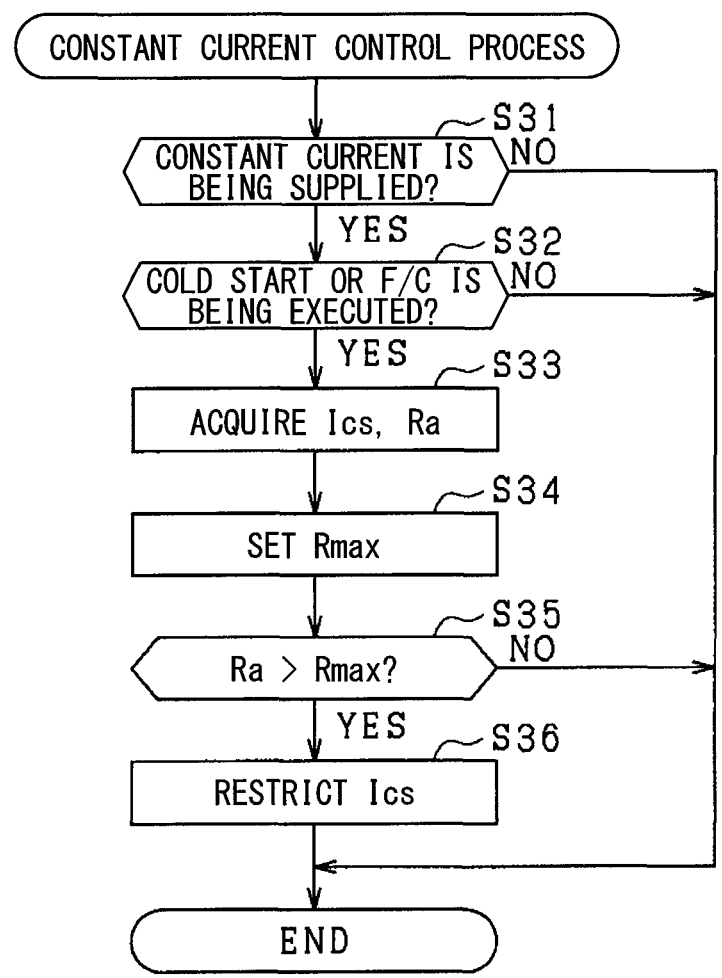
FIG. 12 is a flowchart which shows the constant current control process in a second embodiment.

In the second embodiment, for the supply of constant current by the constant current circuit 43, an allowable resistance range for the element resistance in which the supply of constant current is allowed is set. When the element resistance Ra is determined to be larger than an allowable range, the constant current supplied by the constant current circuit 43 is restricted for the reason that a bad influence on the solid electrolyte layer 32 may occur. The concrete arrangement is described below. In this example, the constant current is set as a variable according to the engine operation condition, etc. FIG. 12 is a flowchart which shows the constant current control process and this process is repeated by the microcomputer 41 in a given cycle.

Figure 13:
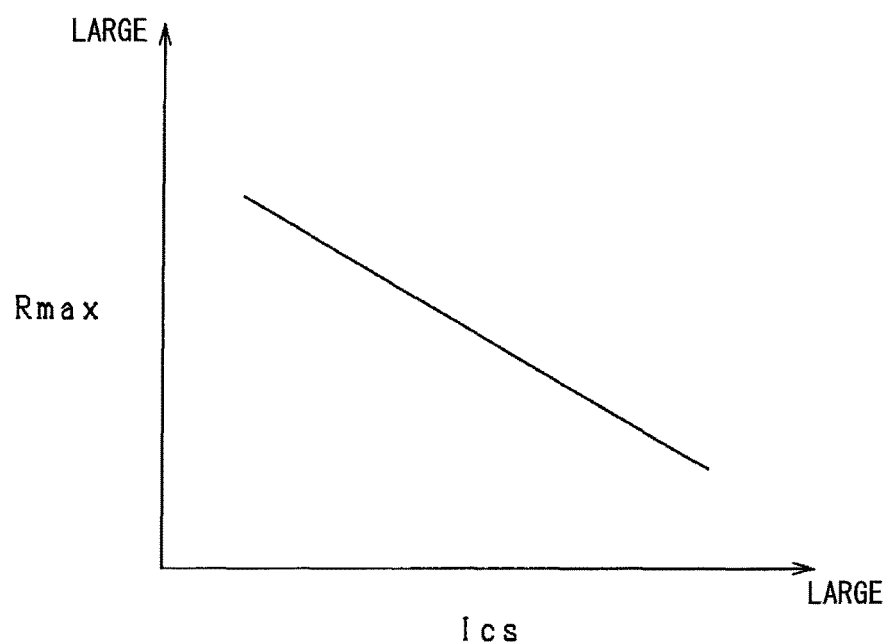
FIG. 13 is a graph which shows the relation between constant current and resistance upper limit.

In FIG. 12, at S31 the microcomputer 41 determines whether or not the constant current is being supplied by the constant current circuit 43. At S32, the microcomputer 41 determines whether or not cold start of the engine 10 or fuel cut is being executed. When NO at S31 or S32, the microcomputer 41 ends this process; or when YES at both S31 and S32, it proceeds to the next step S33. In this embodiment, the step S32 corresponds to a condition determining section. At S33, the microcomputer 41 acquires the present values of constant current Ics and element resistance Ra. At this time, the present value of constant current Ics is set by the microcomputer 41 according to the engine operation condition such as the engine rotation speed or engine load. In this embodiment, the step S33 corresponds to a constant current setting section. After that, at S34 the microcomputer 41 sets the resistance upper limit Rmax which defines the allowable resistance range according to the value of constant current Ics. At this time, the resistance upper limit Rmax is set, for example, using the relation in FIG. 13. According to FIG. 13, when the constant current Ics is larger, the resistance upper limit Rmax is set at a smaller value.

After that, at S35 the microcomputer 41 compares the element resistance Ra and the resistance upper limit Rmax and determines whether Ra>Rmax or not. When Ra≤Rmax, the microcomputer 41 determines that the ongoing constant current supply by the constant current circuit 43 is allowable and ends this process. When Ra>Rmax, the microcomputer 41 proceeds to S36 and restricts the ongoing constant current supply for the reason that a bad influence on the solid electrolyte layer 32 may occur. At this time, the microcomputer 41 decreases the constant current Ics supplied by the constant current circuit 43. In this embodiment, the step S35 corresponds to an influence determining section and a resistance determining section and the step S36 corresponds to a current control section.

When it is determined that the element resistance Ra is larger than the resistance upper limit Rmax, the supply of constant current is restricted. Consequently the constant current can be supplied appropriately according to the relation between element resistance Ra and resistance upper limit Rmax. Also, the constant current is set as a variable according to the engine operation condition and when Ra>Rmax, the constant current is restricted. Consequently not only the constant current can be controlled appropriately according to the operation condition of the engine 10 but also the voltage applied to the sensor element 31 is prevented from becoming excessive even when the constant current Ics is relatively large during high speed rotation or high load.

(Third Embodiment)

In the third embodiment, the gas sensor on the upstream of the first catalyst 15a in FIG. 1 is an $O_2$ sensor 16A of the same electromotive force output type as the $O_2$ sensor 17 on the downstream. The ECU 25 performs air-fuel ratio feedback control according to detection signals from the two $O_2$ sensors 16A and 17A on the upstream and downstream with the first catalyst 15a between them. In this case, the ECU 25 performs main feedback control so that the front air-fuel ratio detected by the upstream $O_2$ sensor 16A becomes a target air-fuel ratio (for example, theoretical air-fuel ratio), and also performs sub-feedback control to set the delay time from when the front air-fuel ratio becomes rich or lean until it is actually determined to be rich or lean, as a variable according to the rear air-fuel ratio detected by the downstream $O_2$ sensor 17. Next, the main feedback control and sub-feedback control will be briefly explained.

At the time when the rich delay time has elapsed since the output value Va of the upstream $O_2$ sensor 16A corresponding to the front air-fuel ratio became richer than the reference value, the ECU 25 makes a rich determination that the air-fuel ratio has become rich, and at the time when the lean delay time has elapsed since Va became leaner than the reference value, the ECU 25 makes a lean determination that the air-fuel ratio has become lean. In this embodiment, the reference value is, for example, 0.45 V. Then, the ECU 25 increases or decreases the amount of injection correction as the amount of feedback correction by skipping and integration according to the result of lean/rich determination and corrects the amount of fuel injection by the amount of feedback correction. This control corresponds to main feedback control. In sub-feedback control, the ECU 25 controls the rich delay time and lean delay time as variables according to whether the output value Vb of the downstream $O_2$ sensor 17 corresponding to the rear air-fuel ratio is rich or lean. In this case, when the output value Vb is larger than the reference value (rear air-fuel ratio is rich), the ECU 25 at least either decreases the rich delay time or increases the lean delay time. When the output value Vb is smaller than the reference value (rear air-fuel ratio is lean), the ECU 25 at least either increases the rich delay time or decreases the lean delay time.

Figure 14:
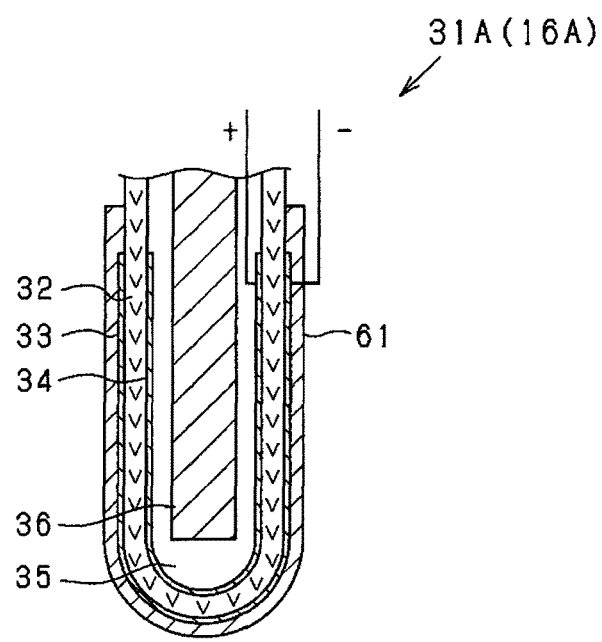
FIG. 14 is a cross sectional view of the sensor element in a third embodiment.

Furthermore, the $O_2$ sensor 16A has a partially modified sensor element structure and the sensor element 31A shown in FIG. 14 has a gas diffusion resistance layer 61 which restricts the diffusion of exhaust gas, on the exhaust side of the exhaust and air sides of the solid electrolyte layer 32. The gas diffusion resistance layer 61 is made of a porous material such as alumina, spinel, or zirconia and located on the outer surface of the sensor element 31 in a manner to cover the exhaust side electrode 33. Consequently, the exhaust gas passes through the gas diffusion resistance layer 61 at a given transmittance and reaches the exhaust side electrode 33.

Figure 15:
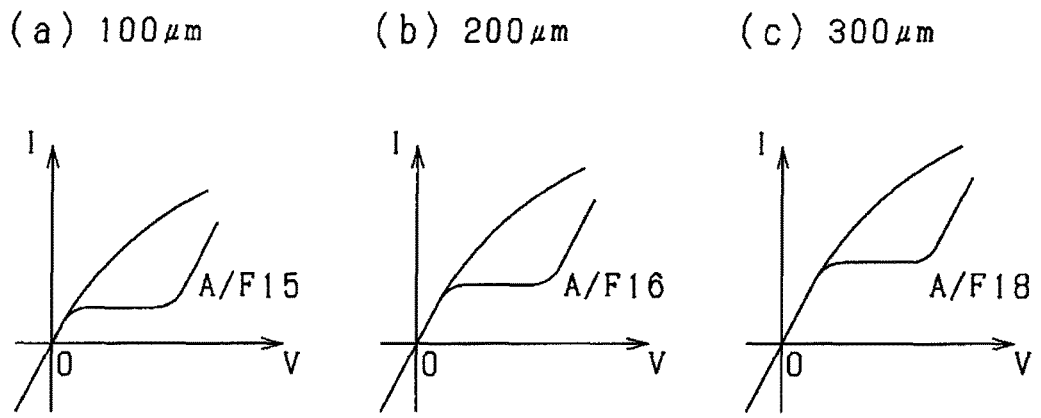
FIG. 15 is a graph which shows the limiting current characteristic of the sensor element.

Although the sensor element 31A structured as mentioned above is basically an electrogenic cell which outputs an electromotive force, it has a limiting current characteristic that it outputs a limiting current depending on the oxygen concentration by applying a voltage between the pair of electrodes 33 and 34. More specifically, the oxygen concentration range as the A/F range, in which limiting current output is possible, changes depending on the thickness of the gas diffusion resistance layer 61, pinhole diameter, etc.; for example, when the gas diffusion resistance layer 61 has a larger thickness, the A/F at which limiting current output is possible is expanded toward the lean side. For example, when the thickness of the gas diffusion resistance layer 61 is 100 µm as shown in FIG. 15(*a*), limiting current output becomes possible at an A/F of 15 or less. When the thickness of the gas diffusion resistance layer 61 is 200 µm as shown in FIG. 15(*b*), limiting current output becomes possible at an A/F of 16 or less. When the thickness of the gas diffusion resistance layer 61 is 300 µm as shown in FIG. 15(*c*), limiting current output becomes possible at an A/F of 18 or less.

In such case, taking the shift of electromotive force output with respect to A/F (λ) by the supply of constant current to the sensor element 31A into consideration, when the thickness of the gas diffusion resistance layer 61 is 100 µm, it is possible to shift the electromotive force characteristic to the lean side by supplying the constant current to the sensor element 31A so that the rich/lean inflection point is A/F=15. When the thickness of the gas diffusion resistance layer 61 is 200 µm, it is possible to shift the electromotive force characteristic to the lean side by supplying the constant current to the sensor element 31A so that the rich/lean inflection point is A/F=16. When the thickness of the gas diffusion resistance layer 61 is 300 µm, it is possible to shift the electromotive force characteristic to the lean side by supplying the constant current to the sensor element 31A so that the rich/lean inflection point is A/F=18.

Summarizing the above, in the sensor element 31A having the gas diffusion resistance layer 61, the amount of shift of the electromotive force characteristic can be expanded by the supply of constant current. In other words, the lean shift amount and the rich shift amount can be expanded. In short, in the $O_2$ sensor 16A located upstream of the exhaust catalyst, the required amount of shift for rich shift or lean shift of the electromotive force characteristic is larger than in the $O_2$ sensor 17 located downstream of the catalyst. On the other hand, in the sensor element 31A which can output an electromotive force and has the gas diffusion resistance layer 61 on the exhaust side of the solid electrolyte layer 32, limiting current output is possible under the condition that a prescribed voltage is applied, and the adoption of this structure makes it possible to expand the amount of shift of the electromotive force characteristic. In such case, even a case that the required amount of rich shift or lean shift of the electromotive force characteristic is large can be addressed appropriately by using the sensor element 31A having the gas diffusion resistance layer 61.

Figure 16:
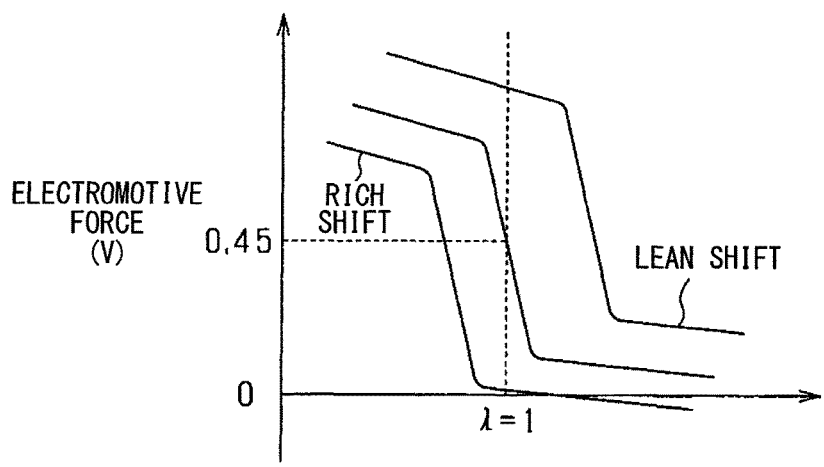
FIG. 16 is an electromotive force graph which shows the relation between air-fuel ratio and the electromotive force of the sensor element.

Furthermore, when the constant current is supplied to the sensor element 31A, rich shift and lean shift occur as illustrated in FIG. 16 which shows details of the electromotive force characteristic. Specifically, when a negative current is made to flow between the pair of electrodes 33 and 34 of the sensor element 31A from the exhaust side to the air side, the electromotive force characteristic of the sensor element 31A shifts to the rich side and conversely when a positive current is made to flow between the pair of electrodes 33 and 34 of the sensor element 31A from the air side to the exhaust side, the electromotive force characteristic of the sensor element 31A shifts to the lean side. In this case, as mentioned above, in the sensor element 31A having the gas diffusion resistance layer 61, the electromotive force characteristic (λ) can be shifted to the rich side and lean side by a maximum of 10% or so. In this embodiment, it is desirable to shift the electromotive force characteristic (λ) about 5%.

For example, in the case of an engine which uses CNG as a gas fuel, it has been confirmed that in order to resolve the deviation between theoretical air-fuel ratio and catalyst window, the electromotive force characteristic of the $O_2$ sensor should be shifted to the rich side about 6%. Also in the case of a lean-combustion engine, it has been confirmed that the electromotive force characteristic of the $O_2$ sensor should be shifted to the rich side about 3-4%.

Figure 17:
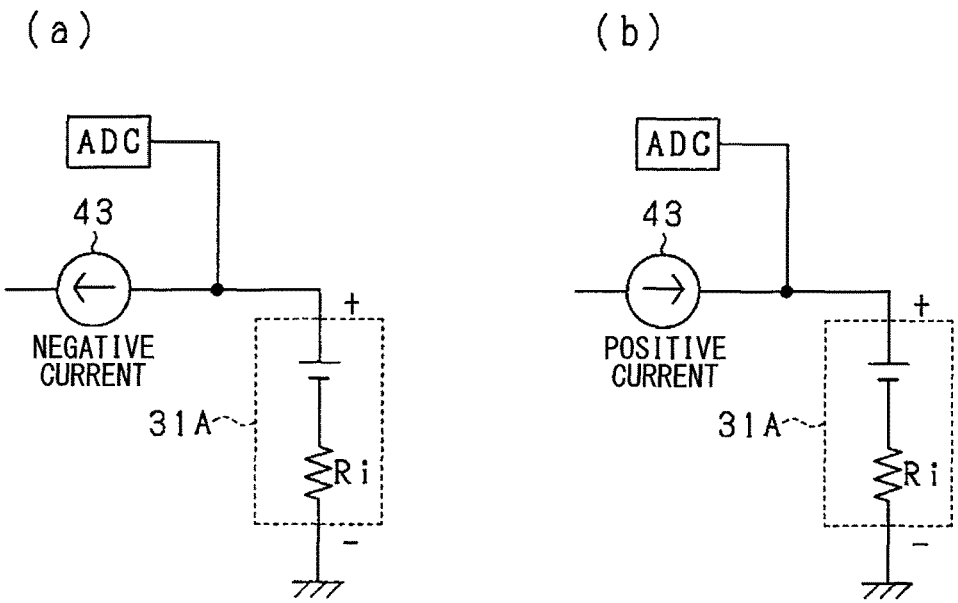
FIG. 17 is an equivalent circuit diagram of the sensor element and its periphery.

In this case, the sensor element 31A has an internal resistance Ri as shown by the equivalent circuit in FIG. 17. Therefore, when a negative current is made to flow in the sensor element 31A as shown in FIG. 17(*a*) in order to shift the electromotive force characteristic to the rich side, the internal resistance Ri causes the electromotive force characteristic as a whole to shift toward the direction in which the voltage is decreased. When a positive current is made to flow in the sensor element 31A as shown in FIG. 17(*b*) in order to shift the electromotive force characteristic to the lean side, the internal resistance Ri causes the electromotive force characteristic as a whole to shift toward the direction in which the voltage is increased.

Here, when the electromotive force characteristic is shifted to the rich side, when the air-fuel ratio is lean, the electromotive force output has a negative value; particularly when the exhaust gas is an air atmosphere, deterioration of the solid electrolyte layer 32, etc. may occur due to increased element stress. Also, when the electromotive force characteristic is shifted to the lean side, when the air-fuel ratio is rich, the electromotive force output becomes excessive, which may cause deterioration of the solid electrolyte layer 32, etc.

For this reason, in this embodiment, a determination is made as to whether the electromotive force characteristic of the sensor element 31A is shifted to the rich side or lean side, and depending on the determination result, the supply of constant current to the sensor element 31A is restricted.

Figure 18:
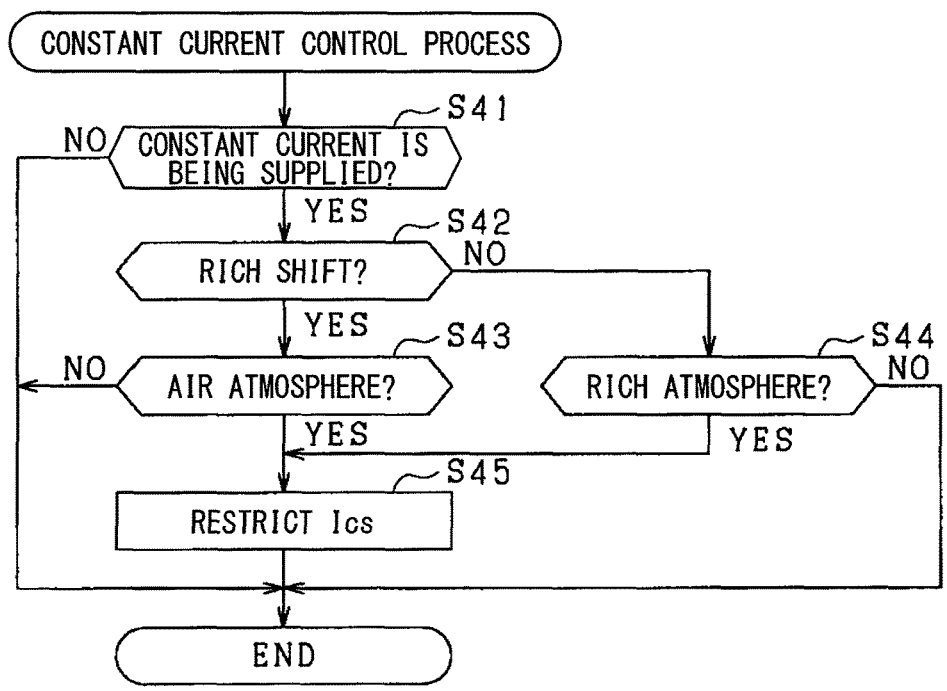
FIG. 18 is a flowchart which shows the constant current control process in the third embodiment.

FIG. 18 is a flowchart which shows the constant current control process in this embodiment and this process is repeated by the microcomputer 41 in a given cycle.

In FIG. 18, at S41 the microcomputer 41 determines whether or not the constant current is being supplied by the constant current circuit 43. When YES, at S42 the microcomputer 41 determines whether or not the electromotive force characteristic of the sensor element 31A is shifted to the rich side. When the microcomputer 41 determines at S42 that the characteristic is shifted to the rich side, it proceeds to S43 and when it determines at S42 that the characteristic is shifted to the lean side, it proceeds to S44.

At S43, the microcomputer 41 determines whether or not the inside of the exhaust pipe 14 has an air atmosphere at the moment. When YES at S43, the microcomputer 41 proceeds to S45 and restricts the ongoing supply of constant current. At S44, the microcomputer 41 determines whether or not the inside of the exhaust pipe 14 has a prescribed rich atmosphere at the moment. When YES at S44, the microcomputer 41 proceeds to S45 and restricts the ongoing supply of constant current. In this case, the microcomputer 41 should restrict the supply of constant current by decreasing the constant current or stopping the supply of constant current. For example, when fuel cut is being executed, the microcomputer 41 determines that the inside of the exhaust pipe 14 has an air atmosphere. Also when acceleration enrichment is being executed, depending on the degree of enrichment, the microcomputer 41 determines that the inside of the exhaust pipe 14 has a rich atmosphere. In this embodiment, the steps S43 and S44 correspond to an influence determining section and the step S45 corresponds to a current control section.

According to this embodiment, with the electromotive force characteristic shifted to the rich side, when the exhaust gas becomes an air atmosphere due to fuel cut, etc., the supply of constant current is restricted, so deterioration of the solid electrolyte layer 32, etc. is suppressed. Also, with the electromotive force characteristic shifted to the lean side, when the exhaust gas becomes a prescribed atmosphere, the supply of constant current is restricted, so again deterioration of the solid electrolyte layer 32, etc. is suppressed.

The amount of shift of the electromotive force characteristic changes depending on the magnitude of the constant current supplied to the sensor element 31A and the possibility of occurrence of a bad influence as the degree of influence on the solid electrolyte layer 32 changes depending on the amount of shift. For this reason, at S43 in FIG. 18 the microcomputer 41 may determine whether or not the amount of rich shift is not less than a prescribed level and the inside of the exhaust pipe 14 has an air atmosphere. Also, at S44 the microcomputer 41 may determine whether or not the amount of lean shift is not less than a prescribed level and the inside of the exhaust pipe 14 has a prescribed rich atmosphere. At S43, the microcomputer 41 may make a determination about a prescribed lean atmosphere, instead of a determination about an air atmosphere.

(Fourth Embodiment)

In the fourth embodiment, when a bad influence on the solid electrolyte layer 32 (deterioration, etc.) may occur, the supply of constant current is stopped to restrict the supply of constant current. In this embodiment, the $O_2$ sensor 16A with a gas diffusion resistance layer (sensor element 31A) is used as a gas sensor on the upstream of the catalyst as in the third embodiment.

Figure 19:
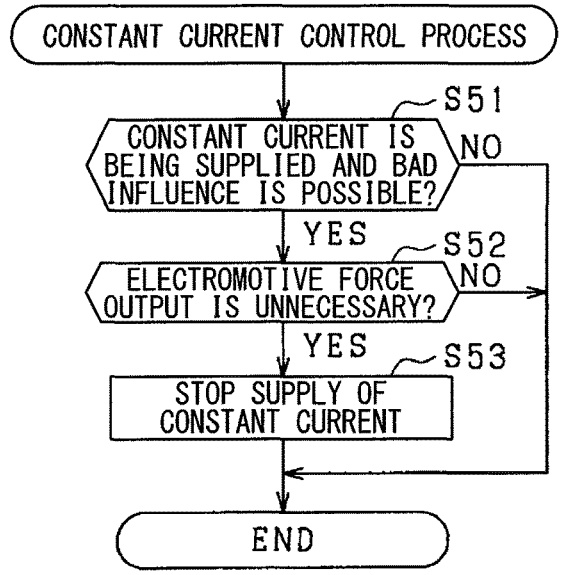
FIG. 19 is a flowchart which shows the constant current control process in a fourth embodiment.

FIG. 19 is a flowchart which shows the constant current control process in this embodiment and this process is repeated by the microcomputer 41 in a given cycle.

In FIG. 19, at S51 the microcomputer 41 determines whether or not the constant current is being supplied by the constant current circuit 43 and a bad influence on the solid electrolyte layer 32 may occur due to the supply of constant current. At this time, when the element resistance of the sensor element 31A is not less than a prescribed level (for example, see S35 in FIG. 12) or the constant current is not less than a prescribed level (for example, see S15 in FIG. 8), the microcomputer 41 determines that a bad influence on the solid electrolyte layer 32 may occur. When YES at S51, the microcomputer 41 proceeds to the next step S52. In this embodiment, the step S51 corresponds to an influence determining section.

At S52, the microcomputer 41 determines whether or not the ongoing engine operation condition is a condition in which electromotive force output by the $O_2$ sensor 16A is unnecessary in control of the operation condition. When YES at S52, the microcomputer 41 proceeds to S53 and stops the supply of constant current. In this embodiment, the step S52 corresponds to a need determining section and the step S53 corresponds to a current control section.

In this embodiment, determination is made as to whether or not electromotive force output by the $O_2$ sensor is necessary in engine control and when electromotive force output is unnecessary, the supply of constant current is stopped. Consequently, even when element stress is large, the period in which the stress is large is shortened as much as possible to protect the sensor element 31.

(Fifth Embodiment)

In the fifth embodiment, stoichiometric control to make stoichiometric combustion with theoretical air-fuel ratio as a target and lean control to make lean combustion with lean air-fuel ratio as a target are switched in controlling the air-fuel ratio of the engine 10. When lean control is performed, it is determined that a bad influence on the solid electrolyte layer 32 of the sensor element may occur and the supply of constant current is stopped. In this embodiment, the $O_2$ sensor 16A with a gas diffusion resistance layer (sensor element 31A) is used as a gas sensor on the upstream of the catalyst as in the third embodiment.

Figure 20:
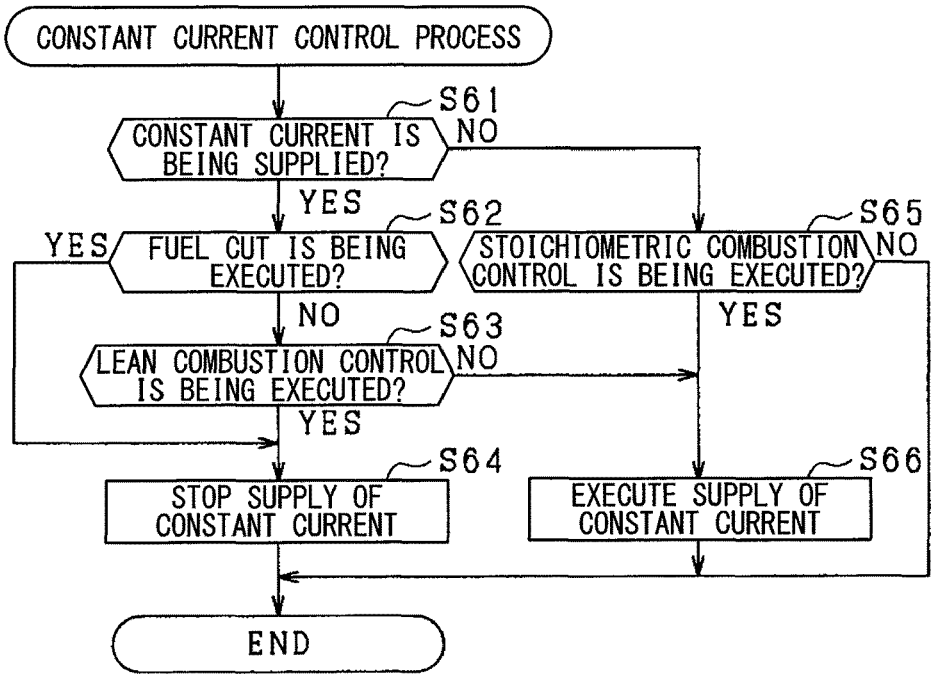
FIG. 20 is a flowchart which shows the constant current control process in a fifth embodiment.

FIG. 20 is a flowchart which shows the constant current control process and this process is repeated by the microcomputer 41 in a given cycle.

In FIG. 20, at S61 the microcomputer 41 determines whether or not the constant current is being supplied by the constant current circuit 43. When YES at S61, the microcomputer 41 proceeds to S62. At S62, the microcomputer 41 determines whether or not fuel cut is being executed. At S63, the microcomputer 41 determines whether or not lean combustion control is being executed. When YES at S62 or S63, the microcomputer 41 proceeds to S64 and stops the supply of constant current. When NO at both S62 and S63, the microcomputer 41 proceeds to S66 and starts or continues the supply of constant current. In this embodiment, the step S63 corresponds to an influence determining section and the step S64 corresponds to a current control section.

When the supply of constant current is stopped, the determination result at S61 is NO and the microcomputer 41 proceeds to S65. At S65, the microcomputer 41 determines whether or not stoichiometric combustion control is being executed. When YES at S65, the microcomputer 41 proceeds to S66 and executes the supply of the constant current.

In short, when fuel cut or lean combustion control is being executed, the air-fuel ratio in the exhaust pipe 14 is lean. Therefore, under the condition that the constant current is supplied to the sensor element 31A, element stress may increase. In this respect, since the supply of constant current is stopped during fuel cut or lean combustion control, the sensor element 31A is protected properly.

In FIG. 20, determination may be made as to whether or not cold start of the engine 10 is being executed, so that when cold start is being executed, the supply of constant current is stopped for the reason that a bad influence on the solid electrolyte layer 32 may occur. Specifically, at S62 the microcomputer 41 determines whether or not cold start is being executed, instead of or in addition to determining whether or not fuel cut is being executed. When YES at S62, the microcomputer 41 stops the supply of constant current.

(Other Embodiments)

The above embodiments may be altered as follows.

In the first and second embodiments, determination is made as to whether cold start of the engine 10 or fuel cut is being executed and when it is determined that cold start or fuel cut is being executed, the supply of constant current is restricted. However, alternatively, the supply of constant current may be restricted regardless of whether or not cold start or fuel cut is being executed. Specifically, S12 in FIG. 8 and S32 in FIG. 12 may be omitted.

The structure of the constant current supplying section is not limited to the above constant current circuit 43 but any structure that can supply a prescribed constant current and vary the value of the current may be adopted. For example, a constant current circuit which can adjust the amount of current by duty control as PWM control may be used. In this case, the constant current may be adjusted as a variable according to a current restriction command.

The gas sensor capable of outputting an electromotive force is not limited to the above $O_2$ sensor 16A or 17; instead the gas sensor may be a so-called 2-cell gas sensor which includes an electrogenic cell and a pump cell. When that is the case, the output characteristic of the electrogenic cell of the 2-cell gas sensor can be changed appropriately and also protection of the gas sensor and proper air-fuel ratio detection can be achieved. Furthermore, not only the cup-shaped structure but also a laminated structure may be used for the electrogenic cell (sensor element).

The $O_2$ sensor having a gas diffusion resistance part may have a structure having pin holes with a prescribed diameter, instead of the structure having a gas diffusion resistance layer with a prescribed thickness.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

The invention claimed is:

1. A gas sensor control device for a gas sensor which has an electromotive cell using a solid electrolyte body and a pair of electrodes placed at a position to interpose the solid electrolyte body, and detects an exhaust gas from an internal combustion engine as an object of a detection and outputs an electromotive force signal depending on an air-fuel ratio of the exhaust gas, the gas sensor control device comprising:
  a constant current supplying circuit supplying a constant current to the electromotive cell;
  a computer programmed to at least perform:
    an influence determination which determines a possibility of an occurrence of a bad influence on the solid electrolyte body due to a supply of the constant current performed by the constant current supplying circuit;
    a current control which restricts the constant current supplied by the constant current supplying circuit when the influence determination determines that the bad influence on the solid electrolyte body may occur; and
    a resistance value calculation which calculates a resistance value of the electromotive cell, wherein
    the influence determination determines the possibility of the occurrence of the bad influence on the solid electrolyte body according to the resistance value of the electromotive cell calculated by the resistance value calculation;
    the influence determination includes
      an allowable value setting which sets, as an allowable value, an upper limit of a current which can be supplied to the electromotive cell, according to the resistance value calculation, and calculated by the resistance value calculation, and
      a current determination which determines whether or not the bad influence on the solid electrolyte body may occur, according to whether or not the constant current supplied by the constant current supplying circuit reaches the allowable value.

2. The gas sensor control device according to claim 1, wherein
  when the constant current supplied by the constant current supplying circuit exceeds the allowable value, the current control decreases the constant current by an amount of a current decrease calculated from an amount of the constant current excess over the allowable value, and restricts the constant current by a decrease of the constant current.

3. The gas sensor control device according to claim 1, wherein the gas sensor control device is configured to further perform:
  a condition determination which determines that a cold start of the internal combustion engine or a fuel cut of the internal combustion engine is being executed, wherein
  the current control restricts supply of the constant current when the cold start or the fuel cut is determined to be executed.

4. The gas sensor control device according to claim 1, wherein the gas sensor control device is configured to further form:
  a condition determining determination which determines that a cold start of the internal combustion engine or a fuel cut of the internal combustion engine is being executed, wherein
  the influence determination determines that the bad influence on the solid electrolyte body may occur when the cold start or the fuel cut is determined to be executed.

5. The gas sensor control device according to claim 1, wherein the gas sensor control device is configured to further form:
  a need determination which determines whether or not an operation condition of the internal combustion engine is a condition in which an electromotive force output of the gas sensor is necessary in a control of the operation condition, when the bad influence on the solid electrolyte body is determined to possibly occur, wherein
  the current control stops the supply of the constant current when the need determination determines that it is not in a state where the electromotive force output of the gas sensor is necessary.

6. A gas sensor control device for a gas sensor which has an electromotive cell using a solid electrolyte body and a pair of electrodes placed at a position to interpose the solid electrolyte body, and detects an exhaust gas from an internal combustion engine as an object of a detection and outputs an electromotive force signal depending on an air-fuel ratio of the exhaust gas, the gas sensor control device comprising:
  a constant current supplying circuit supplying a constant current to the electromotive cell;
  a computer programmed to at least perform:
    an influence determination which determines a possibility of an occurrence of a bad influence on the solid electrolyte body due to a supply of the constant current performed by the constant current supplying circuit;
    a current control which restricts the constant current supplied by the constant current supplying circuit when the influence determination determines that the bad influence on the solid electrolyte body may occur; and
    a resistance value calculation which calculates a resistance value of the electromotive cell, wherein:
    the influence determination determines the possibility of the occurrence of the bad influence on the solid electrolyte body according to the resistance value of the electromotive cell calculated by the resistance value calculation;

the influence determination determines an allowable resistance value range of the electromotive cell allowing a supply of the constant current by the constant current supplying circuit and has a resistance determination determining whether or not the bad influence on the solid electrolyte body may occur, according to whether or not the resistance value of the electromotive cell calculated by the resistance value calculation is within an allowable range, and the current control restricts the constant current supplied by the constant current supplying circuit when the resistance value of the electromotive cell is larger than the allowable range.

7. The gas sensor control device according to claim 6, further comprising:

a constant current setting sets the constant current supplied by the constant current supplying circuit as a variable according to an engine operation condition, wherein the current control restricts the constant current set by the current setting when the resistance value of the electromotive cell is determined to be larger than the allowable range.

8. A gas sensor control device for a gas sensor which has an electromotive cell using a solid electrolyte body and a pair of electrodes placed at a position to interpose the solid electrolyte body, and detects an exhaust gas from an internal combustion engine as an object of a detection and outputs an electromotive force signal depending on an air-fuel ratio of the exhaust gas, the gas sensor control device comprising:

a constant current supplying circuit supplying a constant current to the electromotive cell;

a computer programmed to at least perform:

an influence determination which determines a possibility of an occurrence of a bad influence on the solid electrolyte body due to a supply of the constant current performed by the constant current supplying circuit and a current control which restricts the constant current supplied by the constant current supplying circuit when the influence determination determines that the bad influence on the solid electrolyte body may occur; wherein:

the constant current supplying circuit supplies the constant current so as to shift an electromotive force characteristic indicating a relation between an electromotive force of the electromotive cell and the air-fuel ratio to a rich side, and the influence determination determines that the bad influence on the solid electrolyte body may occur when the exhaust gas is an air atmosphere or a lean atmosphere in a case where the electromotive force characteristic shifted to the rich side.

9. The gas sensor control device according to claim 8, wherein the constant current supplied so as to shift the electromotive force characteristic being a negative current.

10. A gas sensor control device for a gas sensor which has an electromotive cell using a solid electrolyte body and a pair of electrodes placed at a position to interpose the solid electrolyte body, and detects an exhaust gas from an internal combustion engine as an object of a detection and outputs an electromotive force signal depending on an air-fuel ratio of the exhaust gas, the gas sensor control device comprising:

a constant current supplying circuit supplying a constant current to the electromotive cell;

a computer programmed to at least perform:

an influence determination which determines a possibility of an occurrence of a bad influence on the solid electrolyte body due to a supply of the constant current performed by the constant current supplying circuit and a current control which restricts the constant current supplied by the constant current supplying circuit when the influence determination determines that the bad influence on the solid electrolyte body may occur; wherein:

the constant current supplying circuit supplies the constant current so as to shift the electromotive force characteristic indicating the relation between the electromotive force of the electromotive cell and the air-fuel ratio to a lean side, and the influence determination determines that the bad influence on the solid electrolyte body may occur when the exhaust gas is a rich atmosphere in a case where the electromotive force characteristic shifted to the lean side.

11. The gas sensor control device according to claim 10, wherein the constant current supplied so as to shift the electromotive force characteristic being a positive current, the electromotive force characteristic as a whole being shifted toward the direction in which the electromotive force is increased.

12. A gas sensor control device for a gas sensor which has an electromotive cell using a solid electrolyte body and a pair of electrodes placed at a position to interpose the solid electrolyte body, and detects an exhaust gas from an internal combustion engine as an object of a detection and outputs an electromotive force signal depending on an air-fuel ratio of the exhaust gas, the gas sensor control device comprising:

a constant current supplying circuit supplying a constant current to the electromotive cell;

a computer programmed to at least perform:

an influence determination which determines a possibility of an occurrence of a bad influence on the solid electrolyte body due to a supply of the constant current performed by the constant current supplying circuit and a current control which restricts the constant current supplied by the constant current supplying circuit when the influence determination determines that the bad influence on the solid electrolyte body may occur; wherein:

a stoichiometric control where a theoretical air-fuel ratio is used as a target and a lean control where a lean air-fuel ratio is used as a target are performed as air-fuel ratio controls of the internal combustion engine, and when the lean control is performed, the influence determination determines that the bad influence on the solid electrolyte body may occur.

* * * * *